US011473114B2

(12) United States Patent
Bloom et al.

(10) Patent No.: US 11,473,114 B2
(45) Date of Patent: Oct. 18, 2022

(54) PROCESSES FOR OBTAINING COLORS FROM ALGAL BIOMASSES

(71) Applicant: Archer Daniels Midland Company, Decatur, IL (US)

(72) Inventors: Paul Bloom, Forsyth, IL (US); Karen Brown, Decatur, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 54 days.

(21) Appl. No.: 16/607,960

(22) PCT Filed: Apr. 26, 2018

(86) PCT No.: PCT/US2018/029569
§ 371 (c)(1),
(2) Date: Oct. 24, 2019

(87) PCT Pub. No.: WO2018/200811
PCT Pub. Date: Nov. 1, 2018

(65) Prior Publication Data
US 2021/0102228 A1    Apr. 8, 2021

Related U.S. Application Data

(60) Provisional application No. 62/490,373, filed on Apr. 26, 2017.

(51) Int. Cl.
| | |
|---|---|
| *C12P 17/18* | (2006.01) |
| *C12N 1/06* | (2006.01) |
| *C12N 1/12* | (2006.01) |
| *A23L 5/42* | (2016.01) |
| *A23L 5/43* | (2016.01) |
| *A23L 5/46* | (2016.01) |
| *B01J 19/00* | (2006.01) |

(52) U.S. Cl.
CPC ............... *C12P 17/182* (2013.01); *A23L 5/42* (2016.08); *A23L 5/43* (2016.08); *A23L 5/46* (2016.08); *B01J 19/008* (2013.01); *C12N 1/06* (2013.01); *C12N 1/12* (2013.01)

(58) Field of Classification Search
None
See application file for complete search history.

(56) References Cited

U.S. PATENT DOCUMENTS

2010/0151540 A1*  6/2010  Gordon ................ B01F 5/0646
                                                                      435/134
2011/0300568 A1   12/2011  Parsheh et al.

OTHER PUBLICATIONS

Cuellar-Bermudez et al. Microb Biotechnol. Mar. 2015;8(2):190-209. doi: 10.1111/1751-7915.12167. Epub Sep. 15, 2014. (Year: 2014).*
Macias-Sanchez M D et al: "Comparison of supercritical fluid and ultrasound-assisted extraction of carotenoids and chlorophyll a from Dunaliella salina", Talanta, Elsevier, Amsterdam, NL, vol. 77, No. 3, Jan. 15, 2009 (Jan. 15, 2009), pp. 948-952, XP025760488, ISSN: 0039-9140, DOI: 10.1016/J.TALANTA.2008.07.032 [retrieved on Jul. 25, 2008].
Rahimi Masoud et al: "Application of high frequency ultrasound in different irradiation systems for photosynthesis pigment extraction from Chlorella microalgae", Korean Journal of Chemical Engineering, Springer New York LLC, US, KR, vol. 34, No. 4,Jan. 21, 2017 (Jan. 21, 2017), pp. 1100-1108, XP036204434, ISSN: 0256-1115, DOI: 10.1007/S11814-016-0336-7 [retrieved on Jan. 21, 2017].
Lee Andrew K et al: "Microalgal cell disruption by hydrodynamic cavitation for the production of biofuels", Journal of Applied Phycology, Kluwer, Dordrecht, NL, vol. 27, No. 5, Dec. 16, 2014 (Dec. 16, 2014), pp. 1881-1889, XP036053733, ISSN: 0921-8971, DOI: 10.1007/S10811-014-0483-3 [retrieved on Dec. 16, 2014].
Hadiyanto H et al: "Response surface optimization of ultrasound assisted extraction (UAE) of phycocyanin from microalgae Spirulina platensis", Emirates Journal of Food and Agriculture,, vol. 28, No. 4, Apr. 1, 2016 (Apr. 1, 2016), pp. 227-234, XP002776376, DOI: 10.9755/EJFA.2015-05-193.
Papadaki Sofia et al: "Environmental impact of phycocyanin recovery from Spirulina platensiscyanobacterium", Innovative Food Science and Emerging Technologies, vol. 44, pp. 217-223, XP085263351, ISSN: 1466-8564, DOI: 10.1016/J.IFSET.2017.02.014.
Jin-Liang Liu et al: "Optimization of High-Pressure Ultrasonic-Assisted Simultaneous Extraction of Six Major Constituents from Ligusticum chuanxiong Rhizome using Response Surface Methodology", Molecules, vol. 19, No. 2, Feb. 10, 2014 (Feb. 10, 2014), pp. 1887-1911, XP055678911, DOI: 10.3390/molecules19021887.
Wang M et al: "Microalgal Cell Disruption via Ultrasonic Nozzle Spraying", Applied Biochemistry and Biotechnology, Humana Press Inc, New York, vol. 175, No. 2, Nov. 5, 2014 (Nov. 5, 2014), pp. 1111-1122, XP035428928, ISSN: 0273-2289, DOI: 10.1007/S12010-014-1350-Z [retrieved on Nov. 5, 2014].
Furuki et al. "Rapid and selective extraction of phycocyanin from Spirulina platensis with ultrasonic cell disruption", Jan. 23, 2003, Journal of Applied Phycology, vol. 15: pp. 319-324 p. 319, Para [1]; p. 320, Para [1]; p. 320, Full Para [2]; p. 323; Full Para [3]; p. 324, Full Para [1].
Hadiyanto et al. "Phyocyanin extraction from microalgae Spirulina platensis assisted by ultrasound irradiation: effect of time and temperature", Aug. 2016, Songklanakarin J. Sci. Technol., vol. 38(4): pp. 391-398 p. 394, Full Para [5].
"Phycocyanin", Jun. 2016, Wikipedia, pp. 1-2 p. 1, Para [1].
Gerde et al. "Evaluation of microalgae cell disruption by ultrasonic treatment", Sep. 5, 2012, Bioresource Technology, vol. 125: pp. 175-181 Entire Document.

* cited by examiner

*Primary Examiner* — Christian L Fronda
(74) *Attorney, Agent, or Firm* — Andrew F. Nilles

(57) ABSTRACT

The present invention discloses processes for obtaining a color from an algal biomass. The process includes subjecting an algal biomass to cavitation, thus at least partially disrupting cells of the algal biomass and extracting color from the disrupted, algal biomass.

13 Claims, 7 Drawing Sheets

PROCESSES FOR OBTAINING COLORS FROM ALGAL BIOMASSES

CROSS-REFERENCE TO RELATED APPLICATIONS

This application is a national stage entry of International Application No. PCT/US18/029569, filed Apr. 26, 2018, which itself claims priority to U.S. Provisional Patent Application No. 62/490,373, filed Apr. 26, 2017, each of the contents of the entirety of which are incorporated by this reference.

TECHNICAL FIELD

The present invention related generally to colorants. More particularly, the present invention relates to processes for obtaining colorants from cells.

BACKGROUND OF THE INVENTION

*Spirulina* is a blue/green algae that grows in freshwater and marine environments. *Spirulina* contains an edible blue dye (i.e., phycocyanin) that must be liberated from a *Spirulina* cell for use as a colorant. Current methods for lysing cells of *Spirulina* include homogenization, ball milling, sonication, and/or enhancing the media where the *Spirulina* is grown with trace minerals. However, each of these methods suffers from the drawback of requiring a large footprint for use.

*Spirulina* has gained limited approval from the Food and Drug Administration (FDA) for uses in various foods. As *Spirulina* gains approval for use in more foods, demands for more efficient processes of extracting the color from *Spirulina* will grow.

SUMMARY OF THE INVENTION

In each of its various embodiments, the present invention fulfills these needs and discloses various processes for obtaining a color from an algal biomass, as well as the lysed biomasses produced therefrom.

In one embodiment, a process for obtaining a color from an algal biomass comprises subjecting an algal biomass to cavitation, thus at least partially disrupting cells of the algal biomass and extracting color from the disrupted, algal biomass.

DETAILED DESCRIPTION OF THE INVENTION

The present invention utilizes cavitation to lyse algal cells. Cavitation units typically have a small footprint as compared to other methods used for cell rupture. Cavitation units use forced cavitation over an orifice which results in cell rupture and require little maintenance.

In one embodiment, a process for obtaining a color from an algal biomass comprises subjecting an algal biomass to cavitation, thus at least partially disrupting cells of the algal biomass. The color may be extracted from the disrupted, algal biomass. The algal biomass may be of a *Spirulina* origin and the color may be blue such as phycocyanin.

In an embodiment, trace elements are not added to the algal biomass.

In a further embodiment, the process further includes harvesting the algal biomass, suspending the algal biomass in a liquid, and/or separating solids of the disrupted, algal biomass from liquids of disrupted, algal biomass. The liquid may be water or phosphate buffer.

The cavitation of the process may have a pressure of at least 300 psi, at least 500 psi, and even at least 750 psi.

Extracting color from the disrupted, algal biomass may comprise filtering the disrupted, algal biomass.

Subjecting the algal biomass to cavitation may comprise passing the algal biomass through a first orifice of a cavitation unit and a second unit of the cavitation unit. In one embodiment, the first orifice is smaller than the second orifice, and in another embodiment, the first orifice is bigger than the second orifice.

A disrupted biomass, a color, or a combination thereof obtained by the process of any of the embodiments of the present invention are further disclosed. The disrupted biomass may have a mean particle size of between about 3 μm and 30 μm.

In the present invention, algal biomasses (e.g., *Spirulina*) are suspended in a liquid, such as tap water or phosphate buffer, and passed through a cavitation unit at varying pressures from 500-750 psi. In another embodiment, the algal biomass may be a dried or powdered biomass that is suspended in water or a buffer before cavitation.

The invention is further described with the following non-limited Examples.

Example 1

*Spirulina* biomass was suspended in tap water or phosphate buffer at about 15% biomass. The suspended biomass was passed through an Arisdyne controlled flow cavitation unit model no. CM22 (catalog no. CWDSH3558t-2)

attached to a pump (MO3EHSJSSSMK) at varying pressures ranging from 500-750 psi. The cavitation unit used to perform the lysis of the present invention had orifices of 11 μm and 66 μm, where the biomasses passed through the smaller orifice first.

Figure 1:
FIG. 1 depicts a *Spirulina* biomass of the present invention before being passed through a cavitation unit.
Figure 2:
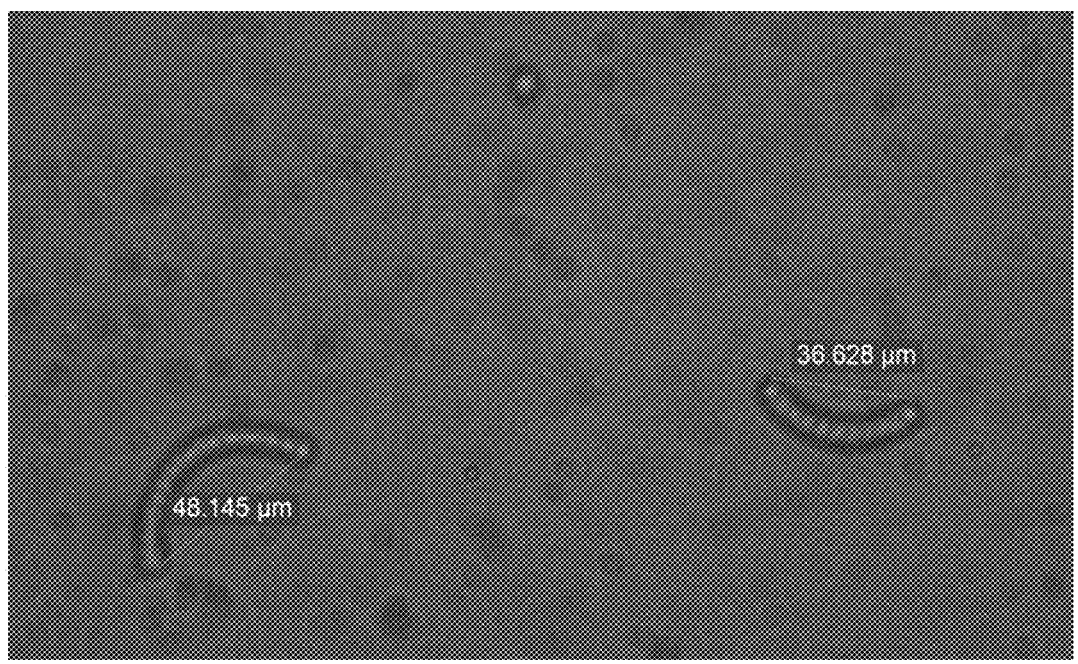
FIG. 2 illustrates one embodiment of the lysed *Spirulina* biomass of the present invention after being passed through a cavitation unit at 500 psi.

Light phase microscopy was used to visualize various *Spirulina* biomasses of the present invention. A sample of the feed *Spirulina* biomass before being passed through the cavitation unit is shown in FIG. 1. A sample of the *Spirulina* biomass after being passed one time through the cavitation unit at 500 psi is shown in FIG. 2. A sample of the *Spirulina* biomass after being passed one time through the cavitation unit at 700 psi is shown in FIG. 3.

Figure 3:
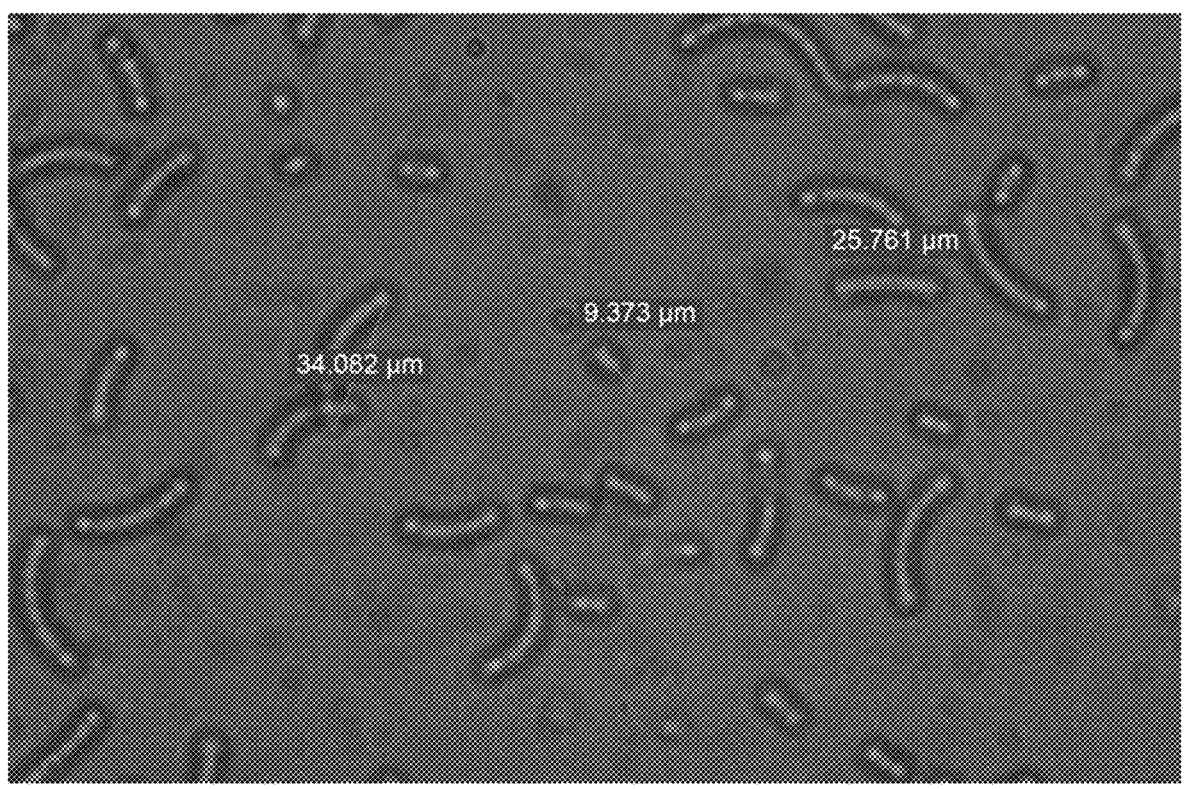
FIG. 3 illustrated another embodiment of the lysed *Spirulina* biomass of the present invention after being passed through a cavitation unit at 700 psi.

FIGS. 1-3 illustrate the ability of cavitation to reduce the whole *Spirulina* cells of FIG. 1 from a cell size of about 170 μm, to about 48 μm from 500 psi cavitation as shown in FIG. 2, and down to about 9 μm from 700 psi cavitation as shown in FIG. 3. FIGS. 2 and 3 verify the ability of cavitation to lyse the *Spirulina* cells.

Example 2

The lysed biomasses were centrifuged and filtered to produce a product having a blue tint. The product having the blue tint may be used as a colorant or further processed to yield a more purified colorant.

Example 3

A spray dried *Spirulina* powder was combined with water or a phosphate buffer solution to produce a slurry having 4% dry solids. The slurry was passed through a cavitation unit substantially as described in Example 1 at varying pressures of 100, 300, or 500 psi. The cavitation liberated the phycocyanin from the spray dried *Spirulina* powder. The orifice sizes of the cavitation unit were 65 μm and 11 μm, where the slurry entered the larger orifice first. Table 1 includes the conditions for the cavitation, the particle size before cavitation, and the amount of phycocyanin (PhC) extracted in relation to the biomass.

TABLE 1

| Steep time (hours) | Cavitation Pressure | Temperature | pH | Particle size before cavitation | PhC after cavitation calculator to biomass |
|---|---|---|---|---|---|
| 0 | 100 | ambient | 6.5 | 70.8 | 2.37 |
| 0 | 300 | ambient | 6.5 | 70.8 | 5.03 |
| 0 | 500 | ambient | 6.5 | 70.8 | 5.40 |
| 1 | 100 | 50° C. | 6.5 | 70.8 | 4.11 |
| 1 | 300 | 50° C. | 6.5 | 70.8 | 4.73 |
| 1 | 500 | 50° C. | 6.5 | 70.8 | 7.39 |
| 1 | 100 | ambient | 6.5 | 70.8 | 2.36 |
| 1 | 300 | ambient | 6.5 | 70.8 | 2.18 |
| 1 | 500 | ambient | 6.5 | 70.8 | 2.68 |

Figure 4A:
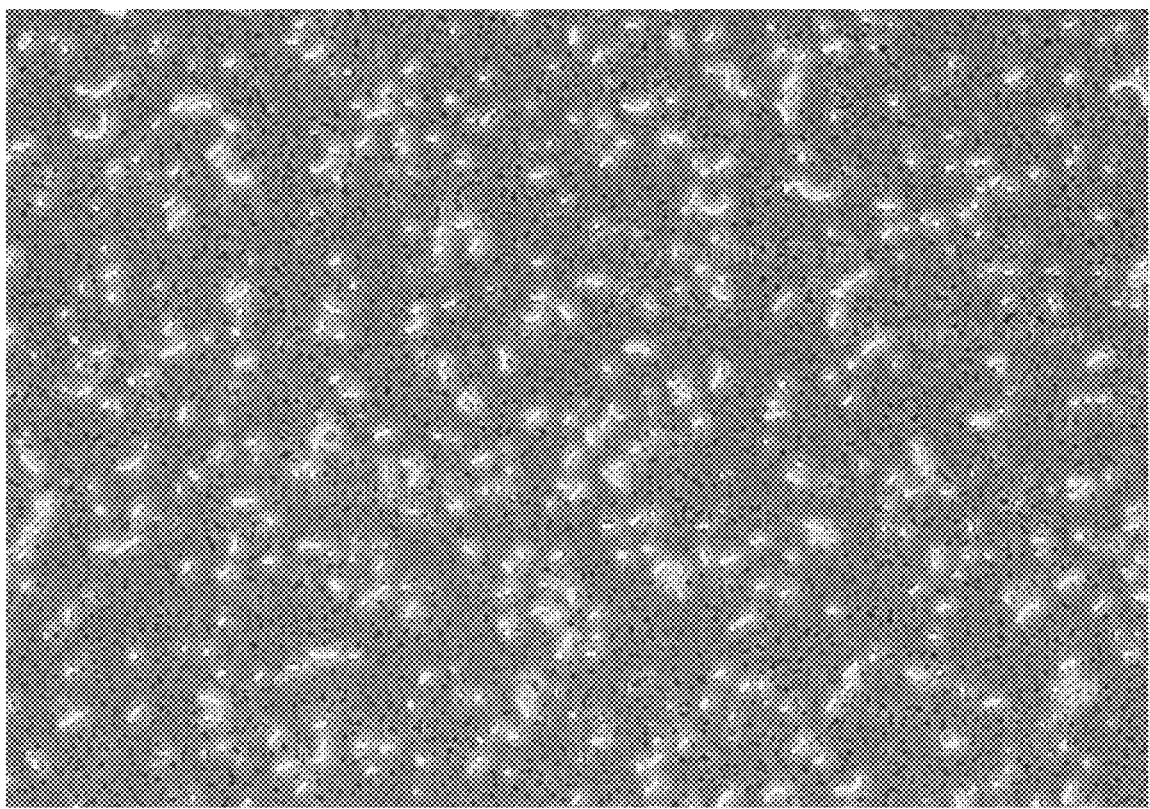
FIGS. 4A and 4B are light microscopy images of various embodiments of lysed *Spirulina* biomasses of the present invention.
Figure 4B:
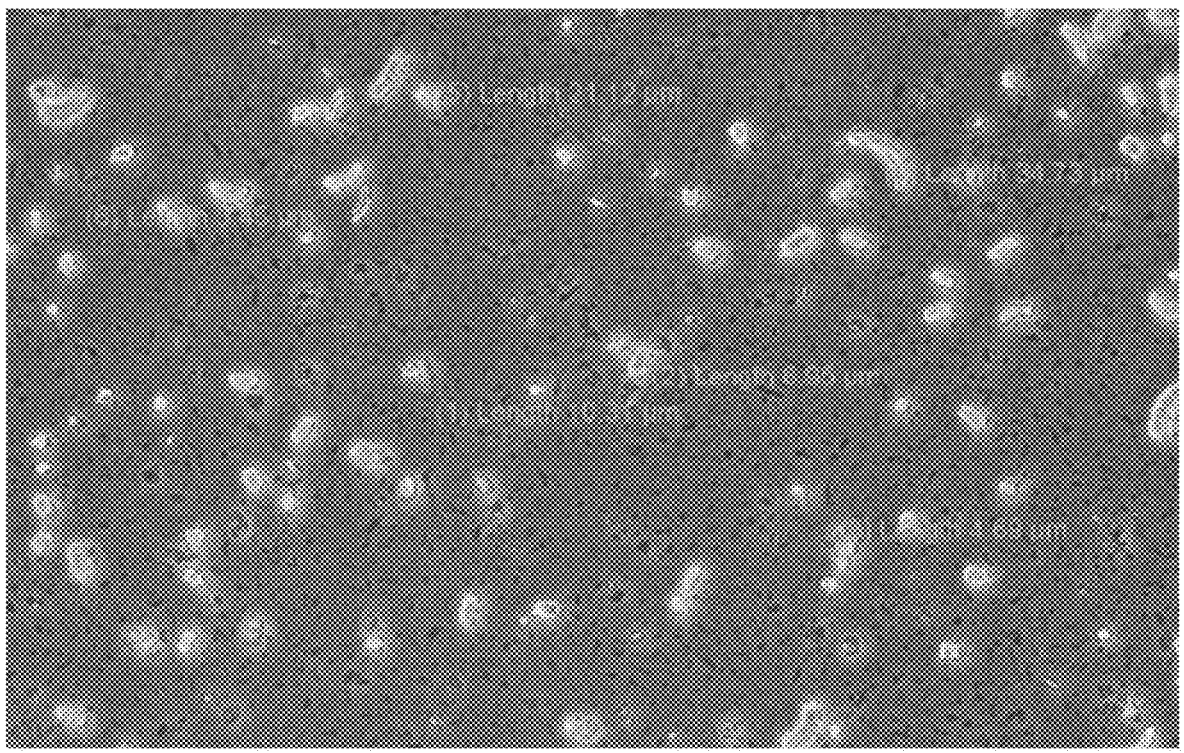
Figure 5A:
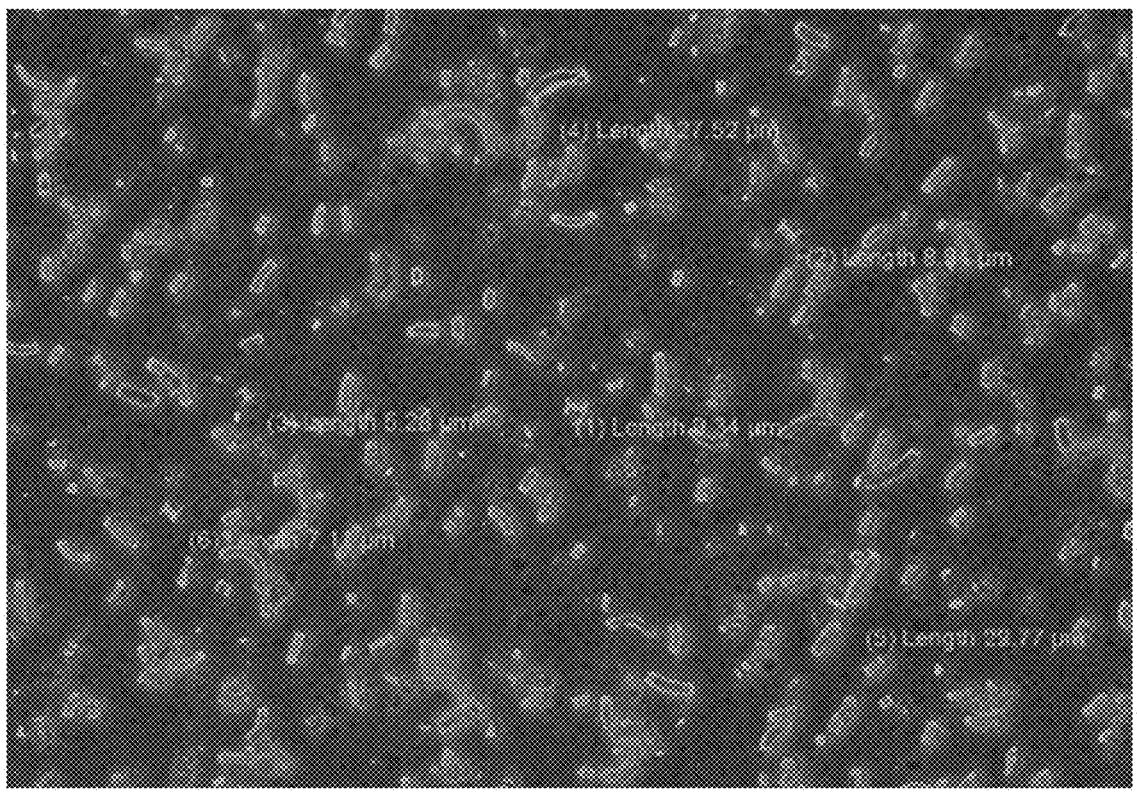
FIGS. 5A and 5B are light microscopy images of additional embodiments of lysed *Spirulina* biomasses of the present invention.
Figure 5B:
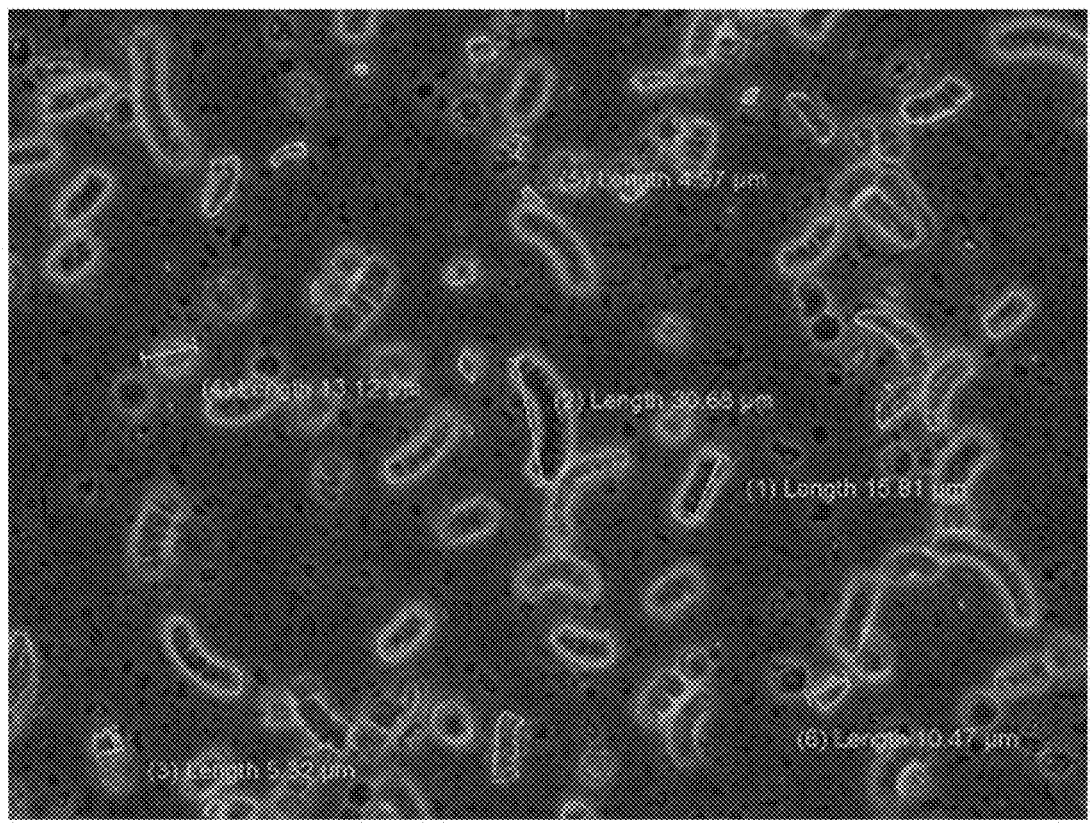

FIGS. 4A and 4B show light microscopy images of the spray dried *Spirulina* after cavitation at 300 psi. FIGS. 5A and 5B show light microscopy images of the spray dried *Spirulina* after cavitation at 500 psi.

Figure 6:
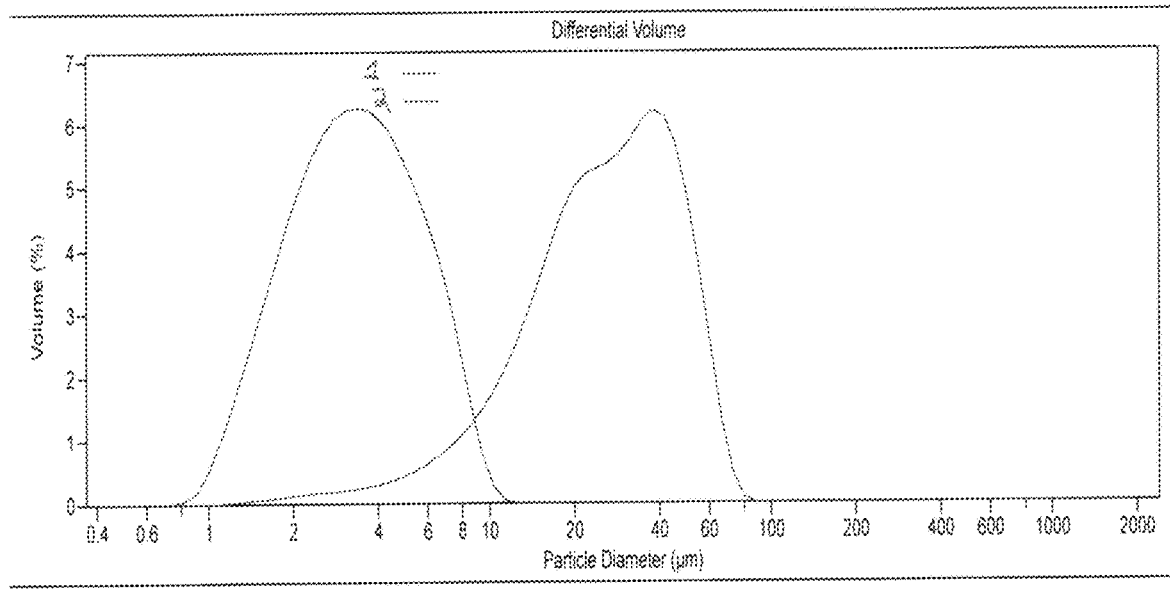
FIG. 6 is a particle distribution of various embodiments of lysed *Spirulina* biomasses of the present invention.

FIG. 6 shows a particle size analysis of various embodiments of the lysed *Spirulina* biomass of the present invention.

Figure 7:
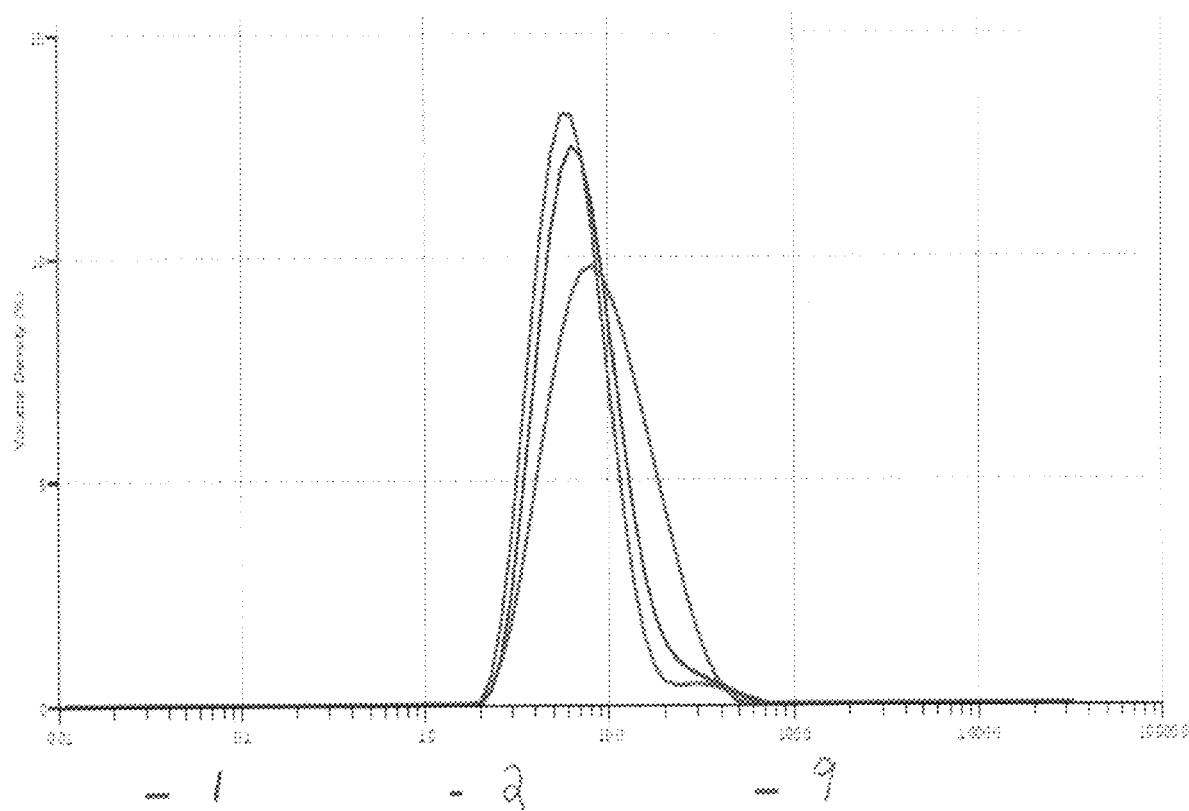
FIG. 7 is a particle distribution of additional embodiments of lysed *Spirulina* biomasses of the present invention.

FIG. 7 illustrates a particle size analysis obtained using the Malvern Mastersizer 3000 on cavitated *Spirulina* samples diluted in water. The lowest peak had a 1 hour steep used in conjunction with the cavitation, the middle peak was cavitated 300 PSI, and the highest peak was cavitated at 500 PSI.

Figure 8:
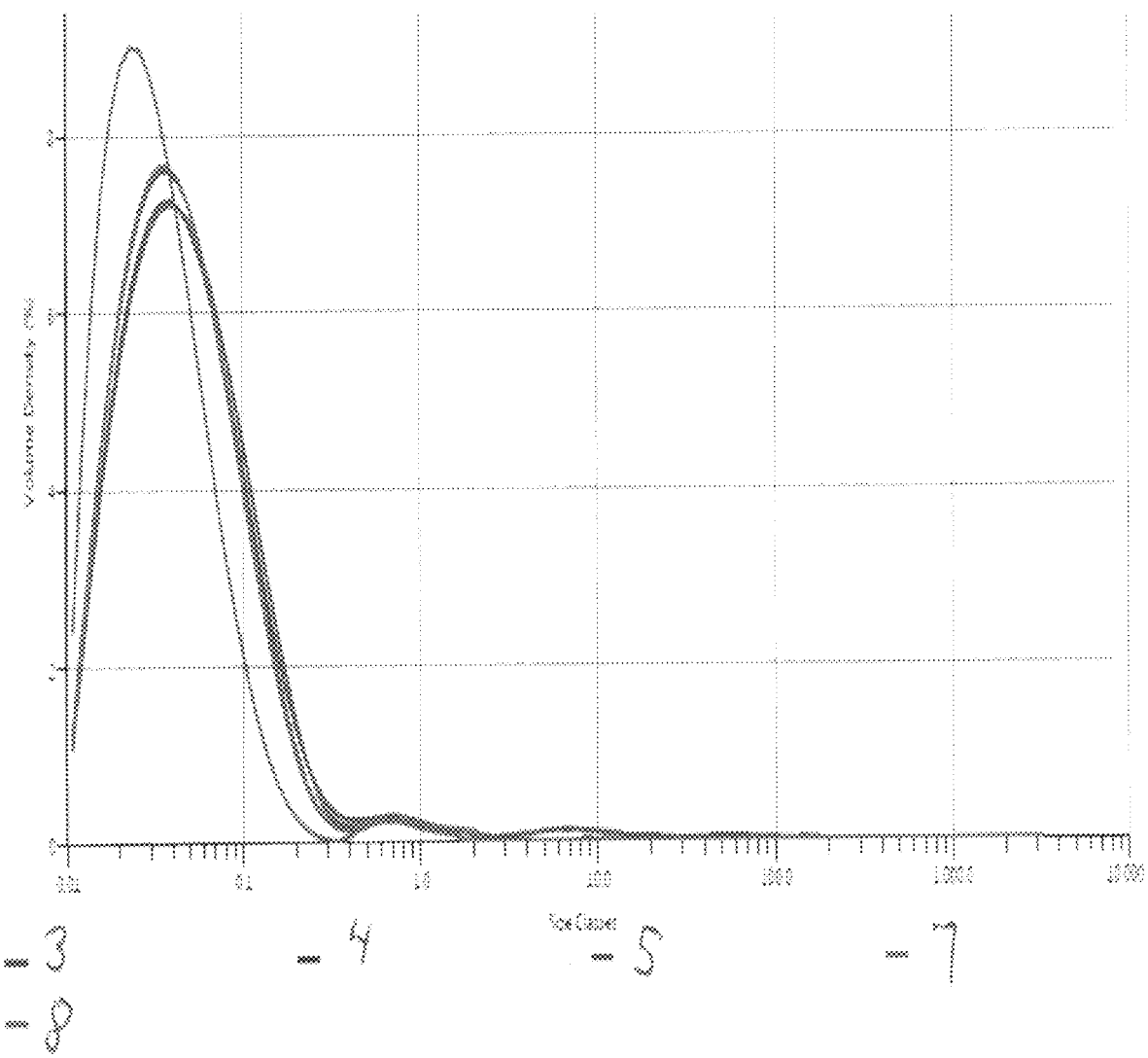
FIG. 8 is a particle distribution of further embodiments of lysed *Spirulina* biomasses of the present invention.

FIG. 8 illustrates a particle size analysis obtained using the Malvern Mastersizer 3000 on cavitated *Spirulina* samples diluted in water. The cavitations were done at either 300 or 500 PSI.

The present invention has been described with reference to certain examples. However, it will be recognized by those of ordinary skill in the art that various substitutions, modifications, or combinations of any of the examples may be made without departing from the spirit and scope of the invention. Thus, the invention is not limited by the description of the examples, but rather by the appended claims as originally filed.

What is claimed is:

1. A process for obtaining phycocyanin from a *Spirulina* biomass, comprising:
   subjecting the *Spirulina* biomass to cavitation, thus at least partially disrupting cells of the *Spirulina* biomass; and
   extracting the phycocyanin from the disrupted, *Spirulina* biomass.

2. The process of claim 1, wherein trace elements are not added to the *Spirulina*-biomass.

3. The process of claim 1, further comprising harvesting the *Spirulina* biomass.

4. The process of claim 1, further comprising suspending the *Spirulina* biomass in a liquid.

5. The process of claim 1, further comprising separating solids of the disrupted, *Spirulina* algal biomass from liquids of disrupted, *Spirulina* algal biomass.

6. The process of claim 1, wherein the cavitation has a pressure of at least 300 psi or at least 500 psi.

7. The process of claim 6, wherein the cavitation has a pressure of at least 750 psi.

8. The process of claim 1, wherein the extracting the phycocyanin from the disrupted, *Spirulina* biomass comprises filtering the disrupted, *Spirulina* biomass.

9. The process of claim 1, wherein the subjecting the *Spirulina* biomass to cavitation comprises passing the *Spirulina* biomass through a first orifice of a cavitation unit and a second unit of the cavitation unit, wherein the first orifice is smaller than the second orifice.

10. The process of claim 4, wherein the liquid is water or phosphate buffer.

11. The process of claim 1, wherein the *Spirulina* biomass is a powder, further comprising suspending the *Spirulina* buffer in water before the cavitation.

12. The process of claim 6, wherein the pressure is between 500-750 psi.

13. The process of claim 1, wherein the at least partially disrupting cells of the *Spirulina* biomass have a mean particle size of between about 3 μm and 30 μm.

* * * * *